United States Patent [19]

Miwa et al.

[11] Patent Number: 4,877,583

[45] Date of Patent: Oct. 31, 1989

[54] FLUORESCENT ANALYZER

[75] Inventors: Harufumi Miwa, Tokyo; Minoru Kashiwada; Ikuo Goto, both of Kawaguchi, all of Japan

[73] Assignee: Ajinomoto Company, Inc., Tokyo, Japan

[21] Appl. No.: 174,818

[22] Filed: Mar. 29, 1988

[30] Foreign Application Priority Data

Apr. 1, 1987 [JP] Japan .................................. 62-77486

[51] Int. Cl.$^4$ ...................... G01N 33/16; G01N 21/00
[52] U.S. Cl. ......................................... 422/73; 356/39; 356/339; 250/461.2; 364/497
[58] Field of Search ............ 356/39, 73, 318, 335–339, 356/343, 364; 250/461.1, 461.2, 573–575; 435/29, 7; 422/73; 436/63; 364/497

[56] References Cited

U.S. PATENT DOCUMENTS

| 4,325,706 | 4/1982 | Gershman et al. | 356/39 |
| 4,435,507 | 3/1984 | Stenkvist | 435/262 |
| 4,455,376 | 6/1984 | Maines | 436/63 |
| 4,492,752 | 1/1985 | Hoffman et al. | 435/7 |
| 4,581,334 | 4/1986 | Kirchanski et al. | 435/29 |
| 4,662,742 | 5/1987 | Chupp | 356/39 |

Primary Examiner—Robert J. Hill, Jr.
Assistant Examiner—T. J. Wallen
Attorney, Agent, or Firm—Oblon, Spivak, McClelland, Maier & Neustadt

[57] ABSTRACT

A fluorescent analyzer including a light source which irradiates a sample with direct light, a first wave selector for passing a predetermined wavelength of light emitted from the light source, a sample cell for holding the sample which is irradiated by light passed by the first wave selector, a second wave selector arranged sidewards of the sample outside a direct path of light from the light source passing straight through the sample for passing light of a second predetermined wavelength emitted from the sample upon irradiation by direct light from the light source, a first light detector for producing a first output signal indicative of the amount of light of the second predetermined wavelength passed by the second wave selector, a second light detector for producing a second output signal indicative of the amount of direct light of the first predetermined wavelength passing straight through the sample, a correction circuit for performing a predetermined correction on the amplitude of the first output signal based on the amplitude of the second output signal to produce a corrected measurement signal, and an indicator for indicating the corrected measurement signal.

1 Claim, 3 Drawing Sheets

FLUORESCENT ANALYZER

BACKGROUND OF THE INVENTION

1. Field of the Invention

This invention relates to a fluorescent analyzer of the type presently utilized in various fields such as clinical analysis, biochemical analysis, precision chemical analysis, etc.

2. Discussion of Background

Various types of fluorescent analyzers have heretofore been developed, typically having an optical system with a basic construction including a light source, a first wave selector, a sample cell, a second wave selector, a light detector, amplifier, an indicator and a recorder. Since fluorescent light is emitted omnidirectionally by the sample upon irradiation with light from the light source, the light detector is arranged to measure fluorescent light emitted sidewards, i.e., in a direction transverse to the incident direction of light from the light source, thereby to minimize the influence of direct light from the light source on the measurement of the fluorescent light from the sample.

However the conventional analyzer experiences a large measurement error when performing measurements on a sample which is not transparent, such as a colored or turbid sample.

SUMMARY OF THE INVENTION

Accordingly, one object of the present invention is to provide a new and improved fluorescent analyzer which overcomes the problem in the prior art fluorescent analyzer and performs accurate measurements despite the color or the turbidity of the sample undergoing measurement.

Another object of this invention is to provide a novel fluorescent analyzer which is capable of correcting for the influence of direct light on the measurement of fluorescent light from the sample based on the absorbance of the direct light, or more particularly, based on the amount of direct light passing straight through the sample.

These and other objects are achieved according to the invention by providing a new and improved fluorescent analyzer including a light source adapted to irradiate a sample with direct light, a first wave selector for passing a first predetermined wavelength of light emitted from the light source, a sample cell for holding said sample, a second wave selector arranged sidewards of the sample cell outside a direct path of light from said light source for passing light of a second predetermined wavelength emitted from the sample upon irradiation by direct light from the light source, a first light detector for producing a first output signal indicative of the amount of light of said second predetermined wavelength passed by said second wave selector, a second light detector for producing a second output signal indicative of the amount of direct light of said first predetermined wavelength passing straight through the sample, a correction circuit for performing a correction of the amplitude of the first output signal based on the amplitude of the second output signal to produce a corrected measurement signal, and an indication means for indicating the corrected measurement signal.

The first wave selector passes from the light emitted by the light source a wavelength to excite a fluorescent matter to be measured in a sample and applies light of the first predetermined wavelength to the sample cell. It typically includes a filter, prism, diffraction grating, chopper and the like. Needless to say, the first predetermined wavelength is determined according to a compound to be measured.

Any shapes available in triangle or the like other than quadrangle may be employed for the sample cell. Further, a flow cell can be used according to the measuring object and other requirements.

The second wave selector passes fluorescent light emitted sidewards from the sample cell selectively to the first light detector, and typically includes a filter, prism, etc. The first light detector translates the received fluorescent light into an electrical signal, for which any phototube, photomultiplier tube and photocell may be used.

The electrical signal generated by the second light detector is amplified by an amplifier and indicated by the indicator means, which may be a display or a recorder, as a fluorescence intensity.

The fluorescent analyzer according to the invention is characterized in that the second light detector is provided on an optical path of the direct light having passed straight through a sample cell, and includes a correction circuit for correcting the intensity of the electrical signal at the output of the first light detector based on the intensity of an electrical signal generated by the second light detector.

As above indicated, the second light detector measures the direct light having passed straight through the sample cell, translates the direct light into an electrical signal and sends it to the correction circuit. Any of phototube, photomultiplier tube and a photocell may also be used as the second light detector.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
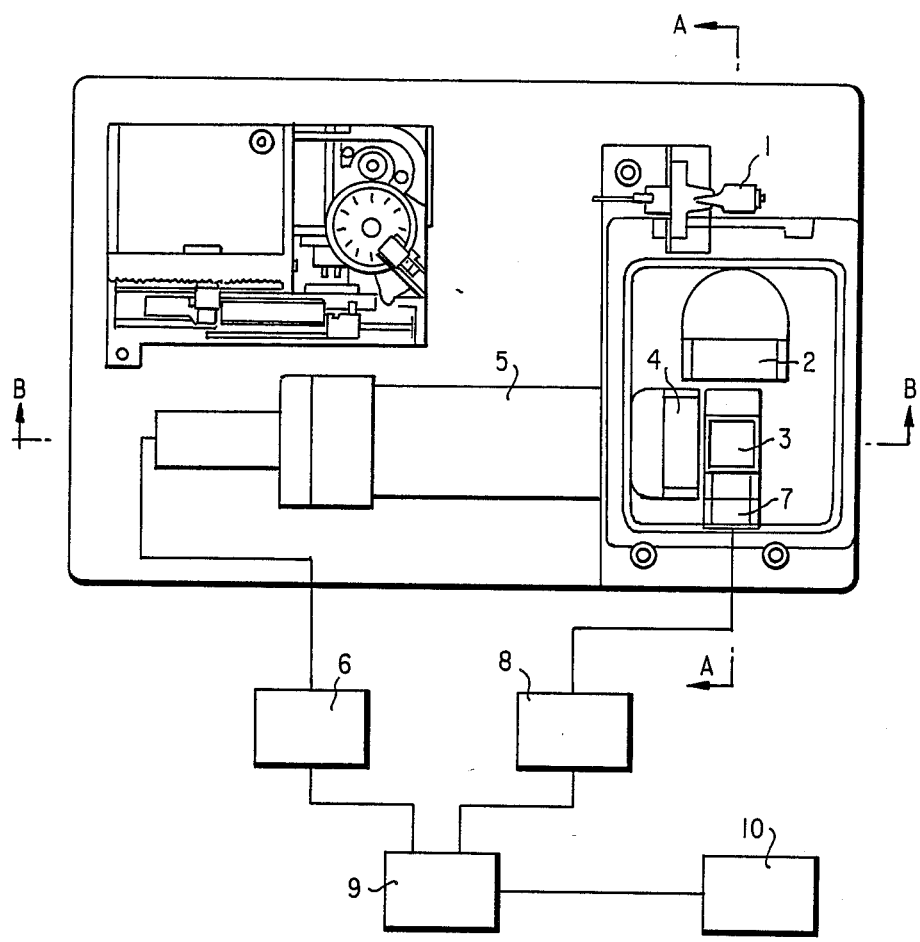
FIG. 1 is a plan view showing the disposition of the main parts of a fluorescent analyzer according to one embodiment of the present invention.
Figure 2:
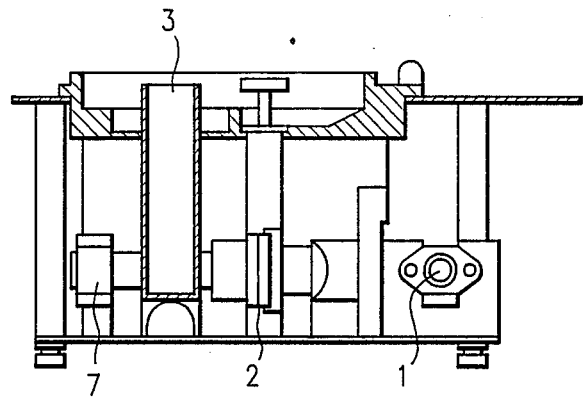
FIG. 2 is a cross-sectional view taken on line A—A of FIG. 1.
Figure 3:
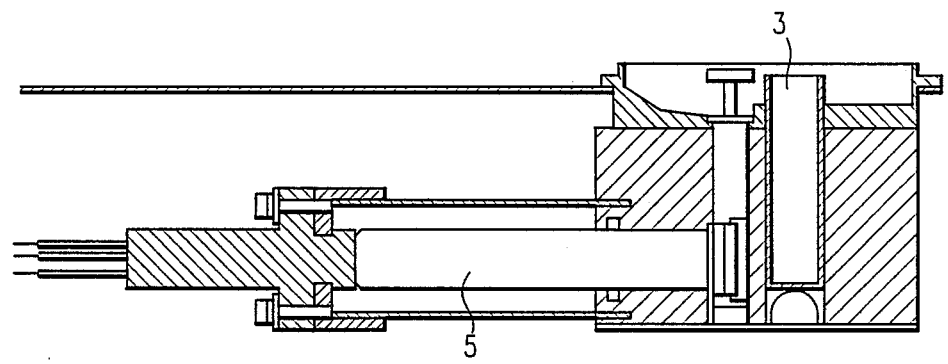
FIG. 3 is a cross-sectional view taken on line B—B of FIG. 1.

Referring now to the drawings, wherein like reference numerals designate identical or corresponding parts throughout the several views, and more particularly to FIG. 1 thereof, the fluorescent analyzer of the present invention includes a light source 1, a wave selector 2, a cuvette (sample cell) 3, a wave selector 4 for selecting a wavelength of the light emitted sidewards from the sample cell, a photomultiplier tube (light detector) 5, an amplifier 6, a photocell (light detector) 7 provided on an optical path of the direct light having passed straight through the sample cell 3, an amplifier 8 of output signals generated therefrom, a correction circuit 9 and a recorder 10.

For measuring a fluorescent matter concentration by means of the fluorescent analyzer, first pure water is put in the cuvette 3 and a lid is shut down, and an auto zero switch (not indicated) is depressed to store the zero point. Next, a first standard solution is put in the cuvette 3 and the lid is shut down, and then a fluorescence STD switch (not indicated) is depressed to store outputs of the photomultiplier tube 5 and the photocell 7. Then, a second standard solution is put in the cuvette 3 and the lid is shut down, and then an absorption STD switch (not shown) is depressed to store outputs of the photomultiplier tube 5 and the photocell 7. A constant k is then calculated and so stored, as discussed hereinafter. Now, everything is ready for measurement, and thus samples will be put in the cuvette 3 one after another for measurement.

The derivation of the constant k is next described in more detail.

First, the first standard solution containing a fluorescent matter to be measured at X mg and being apparently zero in absorbance, or colorless and turbidityless, and the second standard solution (absorbance Y) containing a fluorescent matter to be measured also at X mg and colored or turbid in the same degree as a sample to be tested are prepared, and these are subjected to a measurement on the apparatus of the invention.

With an output (fluorescence value) of the first light detector obtained from the first standard solution designated as $X_1$, an output (absorption value) of the second light detector as $Y_1$, and those obtained from the second standard solution as $X_2$, $Y_2$ respectively, $(X_2-X_1)/(Y_2-Y_1)=k$ is calculated, and k is stored, whereby k is derived and used in subsequent sample measurements.

Color or turbidity of the second standard solution is acceptable if it is comparable with the sample to be tested, and the concentration different from the sample is not significant. In case, for example, a specific component of cow milk is measured, the second standard solution may be prepared by adding cow milk. The first standard solution and the second standard solution do not necessarily have to be the same in the concentration of fluorescent matter, but, coincidence will be effective in obtaining k more simply.

Next, a measurement is carried out one each sample to be tested, and if the output of the first light detector is $X_s$ and the output of the second light detector is $Y_s$, then a correction $X_s-[k(Y_s-Y_1)]=X_s'$ is performed, and $X_s'$ is indicated as the true concentration of the fluorescent matter contained in the samples.

Figure 4:
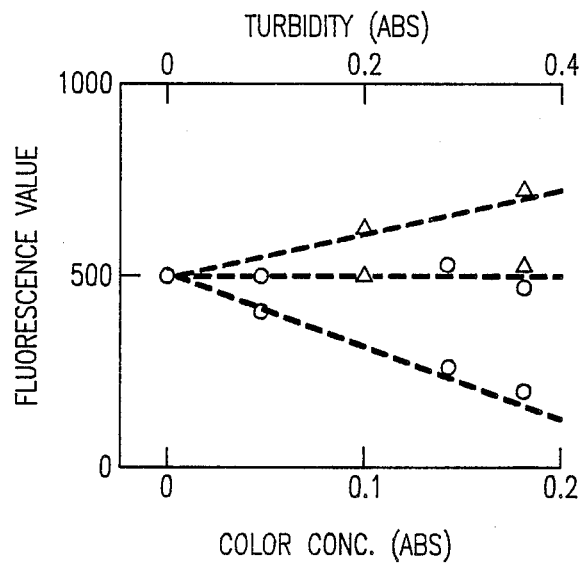
FIG. 4 and FIG. 5 are graphs showing measurement results obtained by means of the fluorescent analyzer of the present invention, with FIG. 4 contrasting the results obtained with the conventional analyzer.
Figure 5:
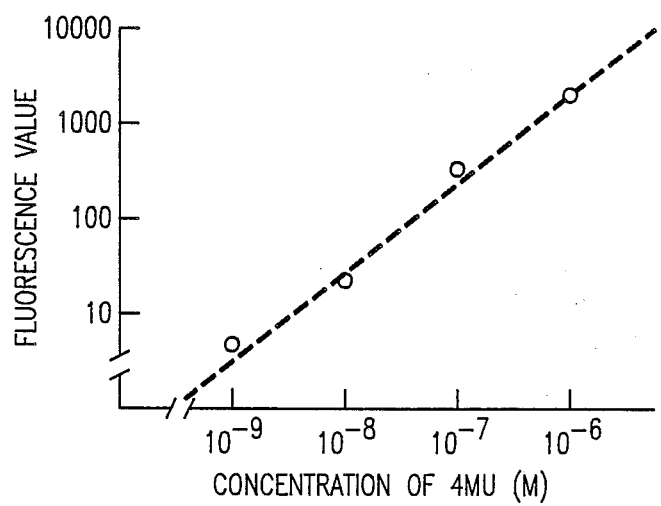

Results obtained through analyzing 4-methyl umbelliferone (4MU) by means of such fluorescent analyzer are shown in FIG. 4 and FIG. 5.

FIG. 4 shows a result obtained through measuring various samples prepared from adding potassium hexacyanoferrate as a coloring matter or powdered milk as a turbid matter in varying concentration in a solution of 4MU dissolved to $10^{-7}$ M by 0.1 M glycineNaOH buffer solution (pH 10). In the drawing, triangular marks and circular marks represent cases where powdered milk and potassium hexacyanoferrate are added respectively, wherein blank ones and dark ones indicate results obtained by means of measurement on the fluorescent analyzer of the invention and conventional fluorescent analyzer, respectively. As indicated, in the case of the conventional fluorescent analyzer, the fluorescence value increases as the turbid matter increases, and the fluorescence value decreases as the coloring matter increases notwithstanding that the 4MU concentration is constant. In case, however, the fluorescent analyzer of the invention is used, it is seen that the fluorescence value does not change despite an increase of the turbid matter or an increase of the coloring matter, and the 4MU concentration can be measured accurately.

Next, a result obtained through measuring 4MU dissolved to various concentrations by the glycine buffer solution with powdered milk further added to various concentrations is shown in FIG. 5. As illustrated, a satisfactory rectilinear relation has been obtained between 4MU and the fluorescence value regardless of the powdered milk concentration.

By using the fluorescent analyzer of the invention, the fluorescent matter concentration to be measured can accurately be measured regardless of presence of coloring matter or turbid matter in a sample. The fluorescent analyzer of the invention is simple to operate and can be manufactured at moderate cost.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A fluorescent anlyzer comprising:
   a light source for irradiating a sample with light;
   a first wave selector for passing a first predetermined wavelength of light emitted from the light source in a path to said sample in a first direction;
   a sample cell for holding said sample in said light path;
   a second wave selector arranged in a second direction perpendicular to said first direction passing light of a second predetermined wavelength emitted in said second direction from the sample upon irradiation by light passed by said first wave selector;
   a first light detector for producing a first output signal indicative of the amount of light of said second predetermined wavelength passed by said second wave selector;
   a second light detector for producing a second output signal indicative of the amount of light of said first predetermined wavelength passing through the sample in said first direction;
   a correction circuit for performing a predetermined correction of an amplitude of the first output signal based on an amplitude of the second output signal to produce a correction measurement signal, said correction circuit performing said correction based on the following relationship:

$Xs'=Xs-[k(Ys-Y_1)]$, where
   $Xs'$=the corrected measurement signal,
   $Xs$=the first output signal obtained from the sample,
   $Ys$=the second output signal obtained from the sample,
   $Y_1$=a predetermined constant, and
   $k$=a predetermined constant; and
   an indication means for indicating the corrected measurement signal.

* * * * *